(12) United States Patent
Brdicko et al.

(10) Patent No.: US 8,215,347 B2
(45) Date of Patent: Jul. 10, 2012

(54) APPARATUS AND METHODS FOR CONTROLLED DEBARKING OF WOOD

(75) Inventors: Jan Brdicko, North Vancouver (CA); Alexander Ryan Precosky, Vancouver (CA); Mehdi Bahrami, Vancouver (CA)

(73) Assignee: FPInnovations, Pointe-Claire (CA)

( * ) Notice: Subject to any disclaimer, the term of this patent is extended or adjusted under 35 U.S.C. 154(b) by 189 days.

(21) Appl. No.: 12/560,165

(22) Filed: Sep. 15, 2009

(65) Prior Publication Data

US 2010/0236664 A1 Sep. 23, 2010

Related U.S. Application Data

(60) Provisional application No. 61/102,655, filed on Oct. 3, 2008.

(51) Int. Cl.
*B27L 1/00* (2006.01)
*B23Q 15/00* (2006.01)

(52) U.S. Cl. ........ 144/340; 144/356; 144/394; 144/404; 144/208.1

(58) Field of Classification Search .......... 144/340, 144/2.1, 3.1, 24.13, 208.1, 208.4, 208.5, 144/208.8, 208.9, 341, 356, 382, 391, 394, 144/402–404
See application file for complete search history.

(56) References Cited

U.S. PATENT DOCUMENTS

| | | | |
|---|---|---|---|
| 4,482,250 A * | 11/1984 | Hirvonen et al. ............. | 356/369 |
| 4,609,019 A | 9/1986 | Hutson | |
| 4,679,475 A | 7/1987 | Antezana | |
| 5,020,579 A * | 6/1991 | Strong ........................... | 144/176 |
| 5,097,880 A | 3/1992 | Pousette | |
| 5,274,244 A * | 12/1993 | Johansson et al. ........ | 250/559.05 |
| 5,887,504 A | 3/1999 | Gombos | |
| 6,526,154 B1 * | 2/2003 | Taipale et al. ................. | 382/100 |
| 6,539,993 B1 | 4/2003 | Starr | |
| 6,546,979 B2 | 4/2003 | Jonkka | |
| 6,971,423 B2 | 12/2005 | Starr | |
| 7,350,548 B1 | 4/2008 | Cholewczynski et al. | |
| 7,431,060 B2 | 10/2008 | Price et al. | |

FOREIGN PATENT DOCUMENTS

| | | |
|---|---|---|
| EP | 0126140 B1 | 2/1987 |
| EP | 1186388 B1 | 8/2004 |
| WO | 8402159 A1 | 6/1984 |
| WO | 9700762 A1 | 1/1997 |
| WO | 9704930 A1 | 2/1997 |
| WO | 2008105963 A2 | 9/2008 |

* cited by examiner

*Primary Examiner* — Shelley Self
(74) *Attorney, Agent, or Firm* — Oyen Wiggs Green & Mutala LLP (57) ABSTRACT

An apparatus for determining one or more optimal operating parameters for debarking wood is provided. The apparatus has a scraper and an actuator configured to adjust the position of the scraper toward a sample portion of the wood to scrape a surface of the sample portion of the wood with a scraping force. The apparatus also has a force sensor operatively associated with the scraper for detecting the scraping force. A light source impinges light on a scraped surface of the sample portion. A light detector detects a light image defined by light from the light source reflected by the scraped surface. A controller is operatively associated with the force sensor and the light detector. The controller has processing means to determine the one or more optimal operating parameters based on signals relating to the scraping force and signals relating to the light image. The one or more optimal operating parameters are relevant to debarking wood proximal to the sample portion.

16 Claims, 8 Drawing Sheets

APPARATUS AND METHODS FOR CONTROLLED DEBARKING OF WOOD

TECHNICAL FIELD

The invention relates generally to apparatus and methods for controlling the debarking of wood.

BACKGROUND

Removing bark from logs, or debarking, is necessary for many industrial uses of wood. In softwood mills, debarking is typically carried out by a ring debarker. Ring debarkers have multiple debarking tools projecting radially inward from a rotating ring. The tips of the debarking tools scrape the surface of individual logs fed through the ring, providing a circumferential scraping action over the surface of the log, tearing the bark from the wood at the cambium layer. A press roll assembly controls the feed speed of the log through the debarker and carries the debarked log downstream for further processing.

Debarking quality can be assessed by various measures including loss of wood fiber, damage to the wood, and bark remaining on the wood. Ensuring that the radial force applied by the debarking tool tips to the log, or debarking force, is appropriate for the log being debarked is important to ensure optimal debarking. Other important operating parameters in addition to debarking force include feed speed of the log through the debarker, and the pressing force applied by the press rolls to the debarked logs. Optimizing these operating parameters can minimize wood fiber loss, damaged wood fiber, and excessive residual bark on the debarked log.

Variations in temperature and moisture content between logs (and even along the length of a particular log) and variation in log species necessitate adjustment of operating parameters to ensure optimal debarking. Logs that are frozen or dry, for example, require application of greater debarking force than logs that are thawed or wet. Temperature and moisture content variations along the length of a particular log can also affect debarking quality. Manual evaluation and adjustment of debarking operating parameters can be imprecise and impractical, particularly in high production, continuous operation environments such as softwood mills.

It is desirable to provide apparatus and methods that automatically and continuously adjust one or more operating parameters of debarking systems to optimize the debarking of logs.

SUMMARY OF THE INVENTION

One aspect of the invention provides an apparatus for determining one or more optimal operating parameters for debarking wood being fed to a debarker. The apparatus has a scraper and an actuator configured to adjust the position of the scraper toward a sample portion of the wood to scrape a surface of the sample portion of the wood with a scraping force. The apparatus also has a force sensor operatively associated with the scraper for detecting the scraping force. A light source impinges light on a scraped surface of the sample portion. A light detector detects a light image defined by light from the light source reflected by the scraped surface. A controller is operatively associated with the force sensor and the light detector. The controller has processing means to determine the one or more operating parameters based on signals relating to the scraping force and signals relating to the light image. The one or more optimal operating parameters are relevant to debarking wood proximal to the sample portion.

Another aspect of the invention provides a method for determining one or more optimal operating parameters for debarking wood being fed to a downstream debarker. The method includes the steps of:
(a) scraping with a scraping force a sample portion of wood to be debarked by the debarker;
(b) impinging light on a scraped surface of the sample portion;
(c) detecting a light image defined by reflected light from the scraped surface; and
(d) determining the one or more optimal operating parameters based on signals relating to the scraping force and signals relating to the light image.

Another aspect of the invention provides an apparatus for continuous real-time optimization of debarking a wood surface with a debarker. The apparatus includes: a light source for impinging light on the wood surface being debarked; a light detector for detecting a light image defined by light from the light source reflected by the wood surface; and a controller operatively associated with the light detector. The controller includes processing means to determine a degree of bark remaining on the wood surface based on signals from the light detector relating to the light image; and transmitting means configured to transmit signals relating to the degree of bark remaining to a controller of the debarker for optimizing one or more operating parameters for further debarking of the wood surface.

Another aspect of the invention provides a method for continuously optimizing debarking of a wood surface with a debarker in real-time. The method includes the steps of:
(a) impinging light on the wood surface being debarked by the debarker;
(b) detecting a light image defined by reflected light from the wood surface;
(c) determining a degree of bark remaining on the wood surface based on the light image; and
(d) adjusting one or more parameters of the debarker and/or a press roll assembly associated with the debarker based on the degree of bark remaining.

Further applications of the invention and features of specific embodiments of the invention are described below.

BRIEF DESCRIPTION OF THE DRAWINGS

In drawings which depict non-limiting embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the description and drawings are to be regarded in an illustrative, rather than a restrictive, sense.

The invention relates generally to apparatus and methods for optimizing debarking. Optimal operating parameters for a debarker and press roll assembly may be determined with reference to the force required to scrape bark from a sample portion of a log before debarking. Debarking may also be optimized by adjusting operating parameters of the debarker and press roll assembly with reference to real-time imaging of the surface of the log as it is being debarked.

Figure 1:
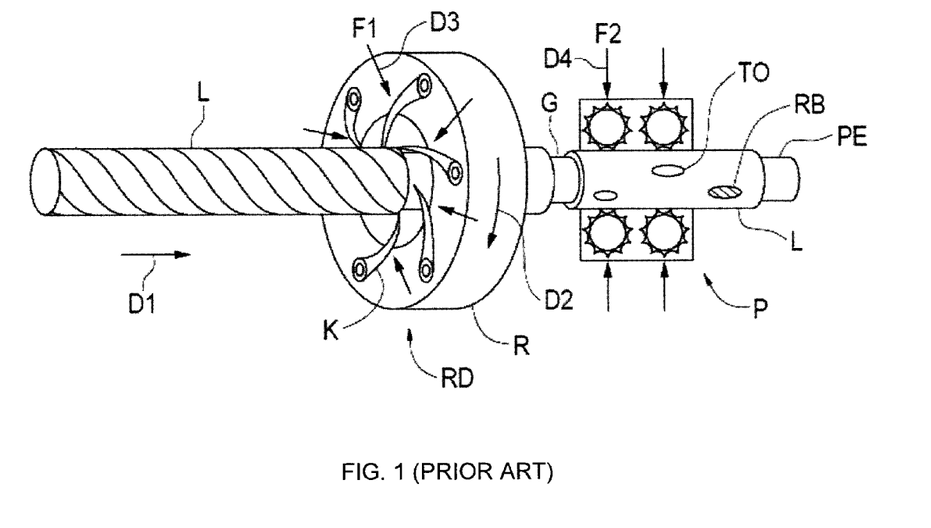
FIG. 1 shows a schematic side view of a known debarking system.

FIG. 1 shows a known debarking system. A log L is fed in direction D1 into ring debarker RD. The feed speed of log L through ring debarker RD is determined by press roll assembly P positioned upstream and downstream of debarker RD (FIG. 1 shows only the downstream assembly). Ring R rotates in direction D2 causing debarking knives K to debark log L with a debarking force F1 radially inward in direction D3. Press roll assembly P carries debarked log L from ring debarker RD downstream for further processing. Press rolls of press roll assembly P press against debarked log L with a pressing force F2 in the direction D4 toward log L. Operating parameters of ring debarker RD and press roll assembly P such as the feed speed, debarking force F1, and pressing force F2 are manually set by a mill operator and are often not adjusted for a particular log L, let alone a particular section of log L. This can result in poor quality debarking evidenced on illustrated log L for example by grooves G, tear outs TO, "pencil ends" PE, and residual bark RB.

Figure 2:
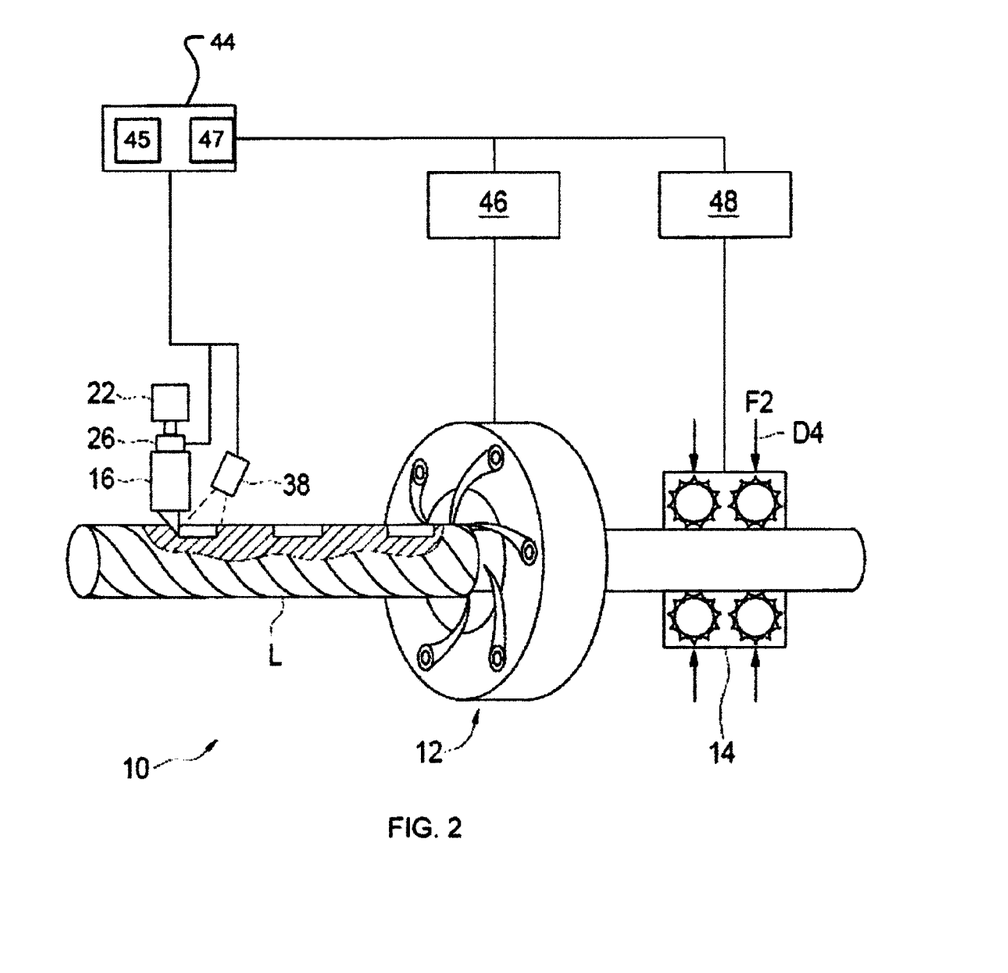
FIG. 2 shows a schematic side view of a debarking system according to one embodiment of the present invention.
Figure 3:
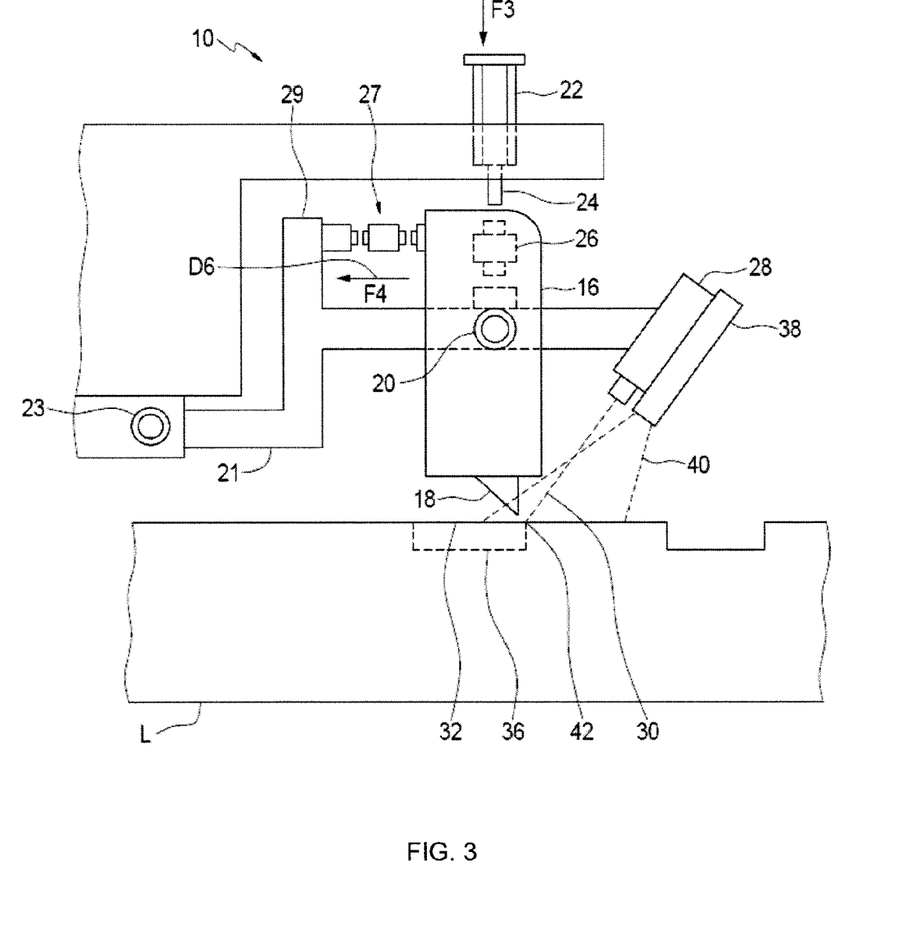
FIG. 3 shows a close-up schematic side view of the embodiment shown in FIG. 2 with the scraper in a retracted position.
Figure 4:
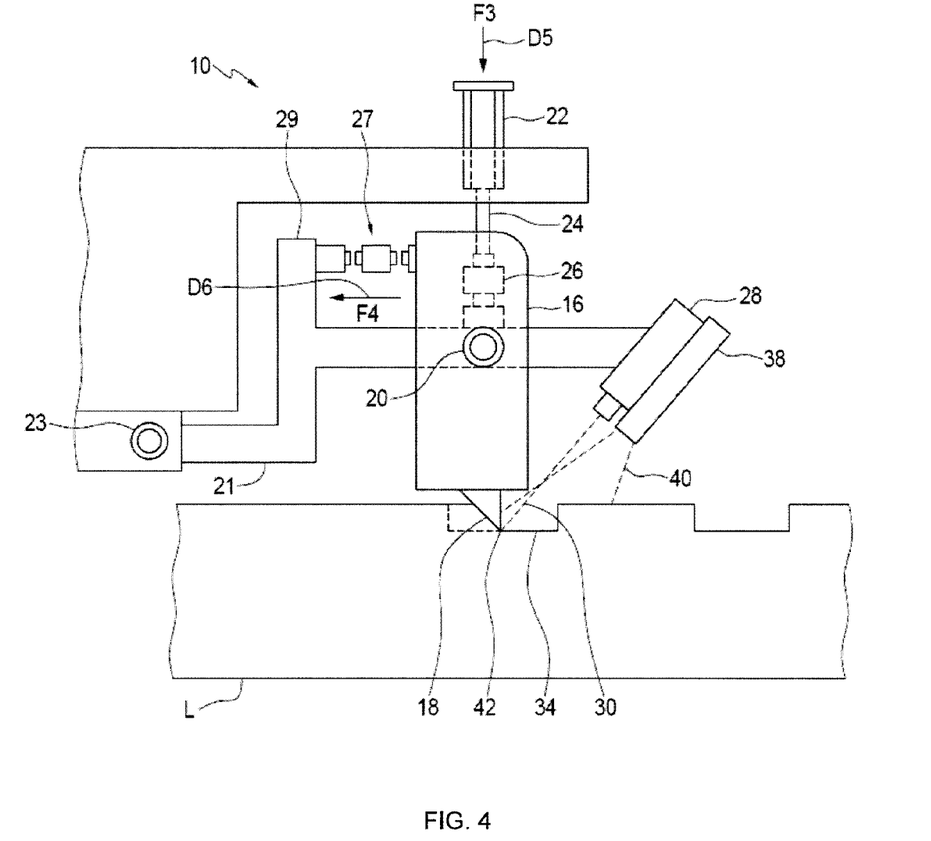
FIG. 4 shows a close-up schematic side view of the embodiment shown in FIG. 2 with the scraper in an extended position.

FIGS. 2 to 4 illustrate one embodiment of the present invention. An apparatus 10 for determining one or more optimal operating parameters for debarking log L is located upstream of a ring debarker 12 and press roll assembly 14. Log L may be any form of wood from which it is desirable to remove bark.

Apparatus 10 has a scraper 16 with a tip 18. Tip 18 may have dimensions similar or identical to the dimensions of the tips of the debarking tools of ring debarker 12. For example, tip 18 may be a square-shaped tip with edges each approximately 2 inches in length. The angle of tip 18 with respect to log L may be similar or identical to the angle at which the tips of the debarking tools of ring debarker 12 engage log L. Tip 18 may be attached to scraper 16 by fastening means, such as screw threads. Scraper 16 is attached to a movable frame 21 at pivot point 20. Movable frame 21 is pivotable at point 23, allowing scraper 16 to move between a retracted position where tip 18 does not contact log L (shown in FIG. 3) and a deployed position where tip 18 scrapes a surface 32 of a sample portion 36 of log L (shown in FIG. 4). Movable frame 21 can be held in the retracted position by actuator 22 via known computer control means.

Actuator 22 has an extendible arm 24 configured to push scraper 16 (and therefore movable frame 21 to which actuator 22 is attached) toward the deployed position. Actuator 22 may be a pneumatic actuator, as in the illustrated embodiment, or any other mechanism suitable to retract and deploy scraper 16.

Force sensor 26 is positioned between actuator 22 and scraper 16. Force sensor 26 detects the amount of force F3 in direction D5 transmitted from actuator 22 to scraper 16 (as shown in FIGS. 3 and 4). Force F3 corresponds to the scraping force substantially perpendicular to log L with which scraper 16 scrapes log L.

Force sensor 27 is positioned between an upper arm 29 of moveable frame 21 and an upper end of scraper 16 distal of pivot point 20 with respect to log L. Force sensor 27 detects the amount of force F4 in direction D6 due to the movement of log L (as shown in FIGS. 3 and 4). Force F4 corresponds to the scraping force substantially parallel to log L with which scraper 16 scrapes log L.

In other embodiments, there may be only one force sensor, or more than two force sensors. The force sensors may be positioned anywhere that experiences strain as a result of engagement of scraper 16 with log L. The positioning of force sensor 26 provides the advantage of direct measurement of force without having to transform or scale the measured force.

Light source 28 directs a light beam 30 onto the surface 32 of the sample portion 36 of log L. As surface 32 is scraped by scraper 16, light beam 30 is directed onto a scraped surface 34 of sample portion 36. Light source 28 may be any light source but preferably one that has long life, remains cool, has low power requirements, and can provide relatively consistent luminous flux within light beam 30 during each acquisition of light image 42. Light source 28 may be a light emitting diode, for example, and may be fitted with lenses or reflectors (not shown) for focusing the light onto the sample portion 36. The wavelength of light source 28 may be a color similarly colored to wood to make efficient use of the light energy, such as red light, as more of the light energy will be reflected rather than absorbed by the log surface 32 or scraped surface 34. A broad-spectrum white light or other light spectrum may be used, especially in the case of the use of a light detector 38 capable of detecting the color content of the reflected light.

Light detector 38 has a field of view 40 for detecting a light image 42 defined by light from light beam 30 reflecting off of surface 32 or scraped surface 34. Light detector 38 may be a high speed digital area or line scan camera. Light detector 38 may be a high speed digital camera with a speed of approximately 50,000 lines per second, for example.

In some embodiments, more than one light source 28 and/or more than one light detector 38 may be provided to provide a more complete view of log L. For example, a single light source 28 and/or single light detector 38 may be blocked by flying debris, a problem that could be addressed by having multiple light sources 28 and/or light detectors 38. Also, light sources 28 and/or light detectors 38 may be arranged at different angles and positions with respect to log L to provide more complete information about log L and the debarking process. In one embodiment, for example, a light source 28/light detector 38 pair could be provided to view a portion of log L that has yet to be scraped, and another light source 28/light detector 38 pair could be provided to view a portion of log L that has already been scraped.

Light detector 38 and force sensor 26 are operatively associated with controller 44 (FIG. 2). The term "operatively associated" as used throughout this specification includes any direct or indirect mechanical or electrical connection that allows relevant communication between components. For example, the connection between actuator 22/light detector 38 and controller 44 may be a hardwire connection or a wireless connection.

Figure 6:
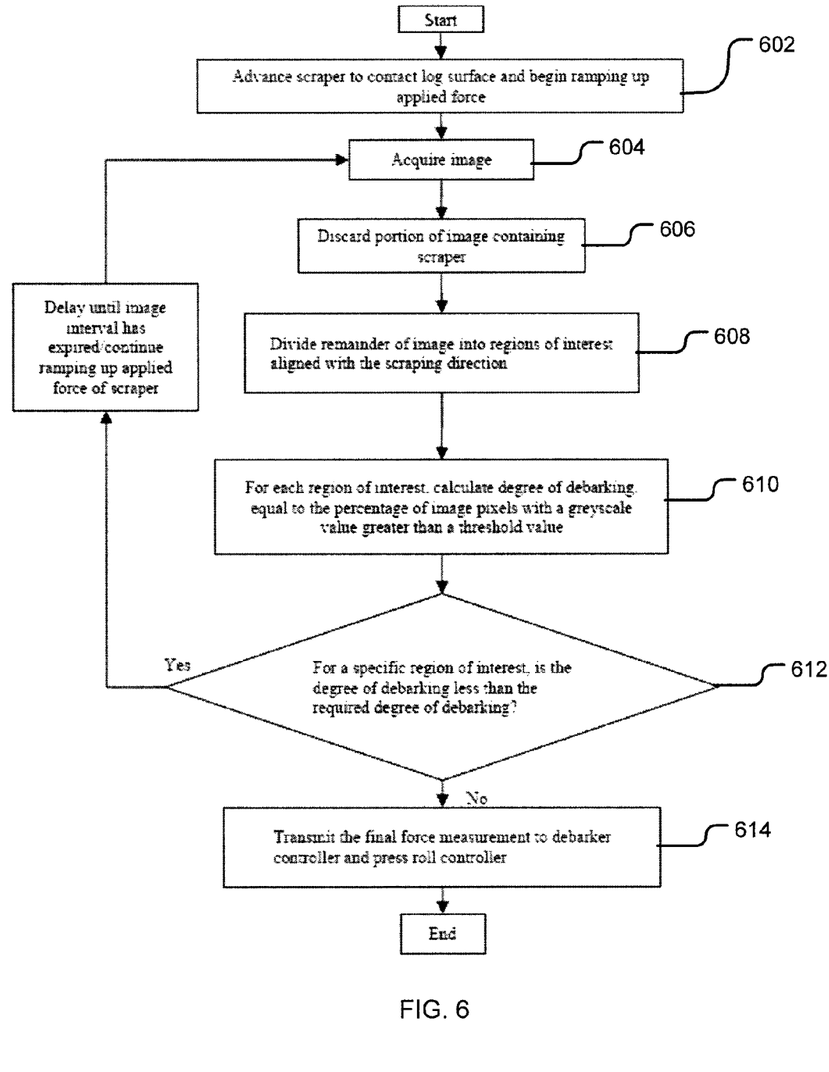
FIG. 6 is a flowchart of a greyscale bark/fibre detection algorithm for measuring optimal debarking force according to one embodiment of the present invention.

Controller 44 comprises processor 45 configured to receive signals from light detector 38 relating to light image 42. Controller 44 is also configured to receive signals from force sensor 26 and/or force sensor 27 relating to scraping force F3 and/or F4. Controller 44 is operatively associated with controller 46 of debarker 12 and controller 48 of press roll assembly 14. FIG. 6 shows an example of an algorithm controller 44 may execute while performing a scrape when using a light detector 38 that produces greyscale images.

In operation, log L is carried to apparatus 10 by known conveying means (not shown). Surface 32 of sample portion 36 of log L is scraped by a tip of scraper 16 to begin removing bark when arm 24 of actuated actuator 22 extends to push scraper 16 (and movable frame 21) to the deployed position with increasing force (step 602 of example algorithm of FIG. 6). Actuator 22 may be configured to be actuated automatically, for example, on a predetermined periodic basis once light detector 38 detects the presence of log L in field of view 40.

The processor 45 of controller 44 determines one or more optimal operating parameters for debarking log L. This is done by first causing actuator 22 to ramp up the scraping force F3 and/or F4 during the course of a scrape to determine the requisite force for removing sufficient bark from sample portion 36 to meet the requisite degree of debarking for the particular end product into which log L is being processed. For example, specifications for a particular end product may require at least 95% of bark to be removed. The processing means 45 will first determine the scraping force F3 and/or F4 of scraper 16 corresponding to the moment when, according to the signals from light detector 38 received by the processor 45, 95% of bark has been removed by scraper 16 at scraped surface 34 of sample portion 36.

The percentage of bark removed from scraped surface 34 can be determined in a number of ways after a light image 42 is acquired (step 604). For example, and although not illustrated in FIG. 6, signals from light detector 38 may relate to dimensions of light image 42. When a concentrated light beam 30 is directed onto scraped surface 34, light image 42 will have different dimensions depending on whether light beam 30 impinges on wood or bark. When light beam 30 impinges on wood fiber, light beam 30 spreads along the grain of the wood fiber creating an elongated light image 42. When light beam 30 impinges on bark, light beam 30 spreads very little, if at all, creating an undistorted light image 42.

Figure 7A:
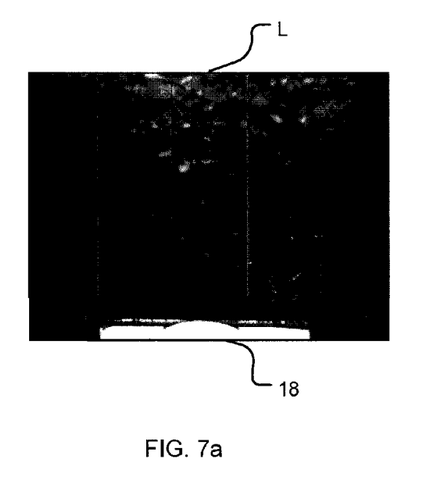
FIG. 7a shows a digital greyscale image obtained by a light detector showing an undebarked log surface according to one embodiment of the present invention.
Figure 7B:
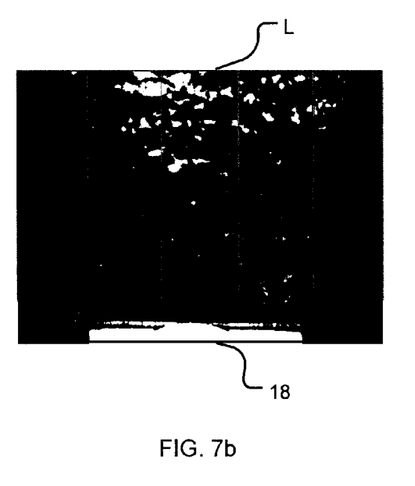
FIG. 7b shows the image of FIG. 7a after a greyscale threshold operation has been performed.
Figure 8A:
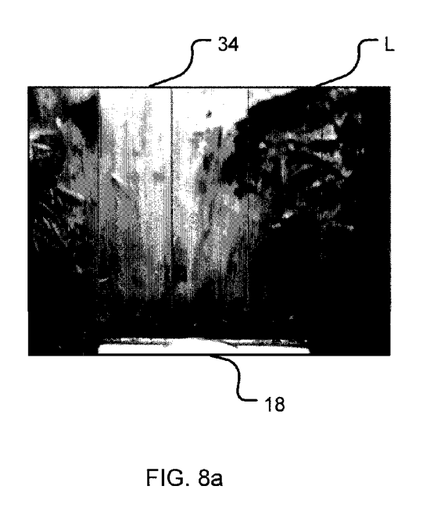
FIG. 8a shows a digital greyscale image obtained by a light detector showing a scraped log surface in which bark has been removed and wood fibre has been revealed according to one embodiment of the present invention.
Figure 8B:
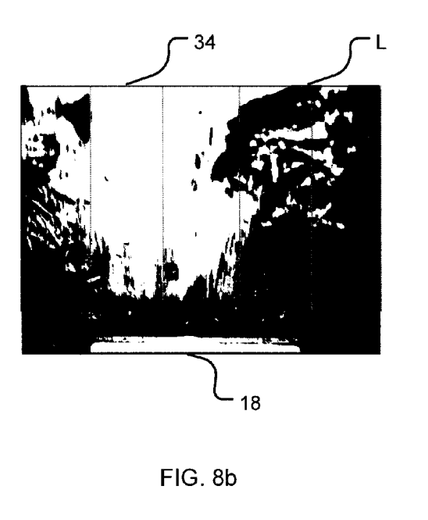
FIG. 8b shows the image of FIG. 8a after a greyscale threshold operation has been performed.

As another example, and illustrated by the example algorithm of FIG. 6, signals from light detector 38 may relate to brightness of light image 42. Since wood fibre reflects more light than bark, the degree of brightness, which may be rendered into greyscale values, provides a measure of the amount of bark remaining on scraped surface 34. Image analysis in this case may be performed by dividing light image 42 into several regions of interest, as shown in FIG. 7a. The bottom rectangle in FIGS. 7 and 8 is ignored as it is occupied by the scraping tip 18 and not of interest (step 606). The remainder of the image is divided into multiple sections (step 608), in this example five rectangular sections. The number of sections may vary, depending on the geometry of scraping tip 18 and diameter of log L. The strip of bark scraped off during the scrape will tend to align along these sections, and each is independently checked for bark removal by the processor 45 of controller 44, although any out of focus section(s) at the periphery of smaller diameter logs may be ignored. Next, a manual threshold is performed on the entire image, that is, a new black-and-white, i.e. not greyscale, image is produced such that:

$$t(i) = \begin{cases} 0 & \text{for } g(i) < k \\ 1 & \text{for } g(i) > k \end{cases}$$

Where k is the threshold value, g(i) is the greyscale value of the pixel before thresholding, and t(i) is the binary value of the pixel after thresholding. The threshold value k is chosen experimentally in a pre-calibration step during apparatus setup, or automatically by using one of several automatic methods known to the field of image processing. Next for each of the sections, the percent coverage of white pixels within that section is calculated and may be considered the percentage of exposed wood fibre (step 610).

Figure 9A:
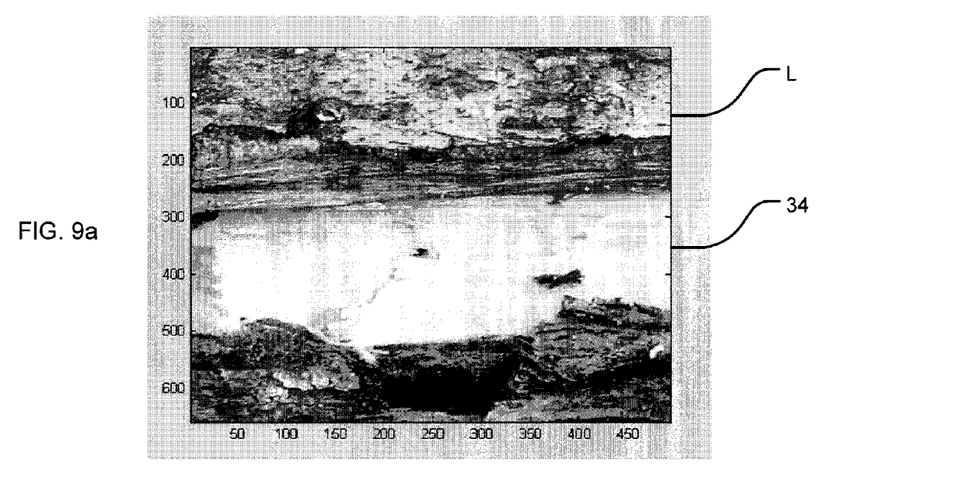
FIG. 9a shows a digital color image obtained by a light detector showing a scraped log surface in which the bark has been removed and the wood fibre has been revealed according to one embodiment of the present invention.
Figure 9B:
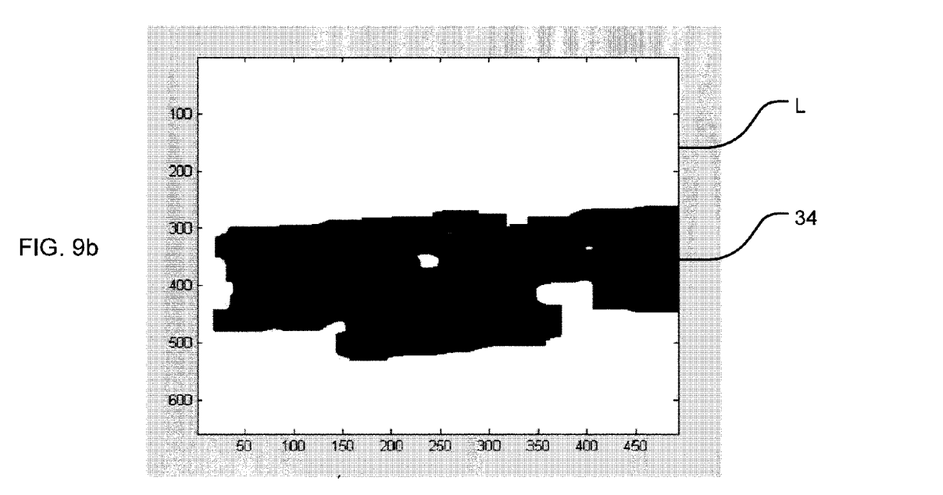
FIG. 9b shows the image of FIG. 9a after a series of processing steps have been performed to detect the amount of revealed wood fibre.

As a further example, light detector 38 may also be capable of generating signals containing the color content of the light to create a colored light image 42 with red, green, and blue color content of the light. Known processors may then detect the color change from bark to wood fibre, providing a measure of the amount of bark remaining on scraped surface 34. A light image 42 captured with a color camera containing both bark and fibre is shown in FIG. 9a. The same image segmented into bark and fibre regions is shown in FIG. 9b. The black region in the middle shows the fibre that was detected. In this example, the image was transformed from the red-green-blue color domain into the hue-saturation-intensity domain, and the saturation channel was blurred with a Gaussian mask to blend similar regions, then a color threshold operation was performed on the saturation channel to segment bark from wood fibre. Other known processors may be used for segmentation of bark and wood fibre.

With any of the means for determining percentage of bark removal, a plurality of images of the scraped surface are rapidly captured by light detector 38 and processed by the processor 45 in order to determine as precisely as possible the moment when the requisite debarking has been achieved (step 612). The image capture rate is chosen to allow many images to be sampled during the time it takes the scraper to ramp up from zero force up to the requisite debarking force. For example, if it takes one second for the force to ramp up to the requisite debarking force, 50 frames during that one second are adequate. A faster debarker would require a camera capable of acquiring images at a faster speed.

Once the relevant scraping force F3 and/or F4 has been determined, the processor 45 of controller 44 calculates the optimal debarking force for debarker 12, the optimal feed speed for log L and/or the optimal pressing force F2 in direction D4 is for press roll assembly 14. The optimal operating parameters are transmitted by transmitter 47 controller 44 to controller 46 of debarker 12 and controller 48 of press roll assembly 14 (step 614). Also once the relevant scraping force F3 and/or F4 has been determined, actuator 22 is configured to retract arm 24, retracting scraper 16 away from log L.

Controllers 46, 48 then optimize their respective operating parameters for the remaining length of log L. In alternative embodiments, controllers 46, 48 may use additional sets of optimal operating parameters received from controller 44 determined from additional sample portions upstream of the first sample portion along log L for debarking portions of log L proximal to the respective additional sample portions, such that a particular log L having n number of scraped sample portions may result in the debarking operating parameters each being optimized up to n number of times for debarking a particular log L.

Figure 5:
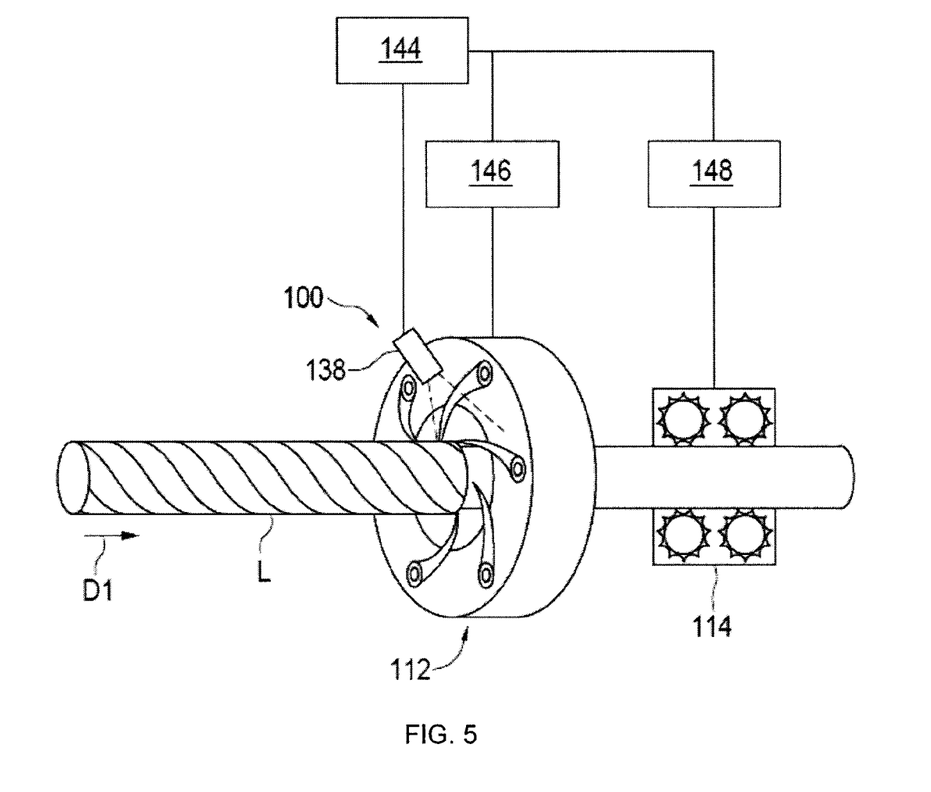
FIG. 5 shows a schematic side view of a debarking system according to one embodiment of the present invention.

Another embodiment of the invention is shown in FIG. 5. An apparatus 100 for continuous real-time optimization of debarking log L with debarker 112 and press roll assembly 114 is shown. Apparatus 100 is positioned within or adjacent to debarker 112. Apparatus 100 includes a light source (not shown), light detector 138 and controller 144. The light source impinges light on a working surface of log L being simultaneously debarked by debarking tools of debarker 112. A light detector 138 detects a light image defined by light from the light source and reflected on the working surface being debarked. Processing means of controller 144 determines the amount of bark remaining, if any, at the working surface of log L (in a similar manner as described above for apparatus 10), and transmits signals relating to the amount of residual bark to controller 146 of debarker 112 and/or controller 148 of press roll assembly 114. Based on the signals, controllers 146, 148 immediately optimize operating parameters of debarker 112 and/or press roll assembly 114.

For example, the signal from controller 144 may indicate that further debarking is required at the working surface. In this case, controllers 146, 148 may increase the debarking force of debarker 112 and/or slow down the feed speed to ensure further debarking at the working surface, for example. If very little or no bark remains at the working surface, then controllers 146, 148 may decrease the debarking force and/or increase the feed speed to minimize damaging the wood fiber at the working surface.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. An apparatus for determining one or more operating parameters for debarking wood being fed to a debarker, the apparatus comprising:
   a scraper;
   an actuator configured to adjust the position of the scraper toward a sample portion of the wood to scrape a surface of the sample portion of the wood with a scraping force;
   a force sensor operatively associated with the scraper detecting the scraping force and generating and sending a signal relating to the scraping force;
   a light source impinging light on a scraped surface of the sample portion;
   a light detector for detecting a light image defined by light from the light source reflected by the scraped surface and generating and sending a signal relating to the light image; and
   a controller operatively associated with the force sensor and the light detector said controller receiving the signal relating to the scraping force and the signal relating to the light image, the controller comprising a processor to determine one or more operating parameters based on the signal relating to the scraping force and the signal relating to the light image, whereby the one or more operating parameters are relevant to debarking wood proximal to the sample portion.

2. An apparatus according to claim 1 wherein the processor is configured to evaluate from the light image a degree of bark remaining on the scraped surface and to determine the one or more operating parameters based on the signals relating to the scraping force when the degree of bark remaining falls below a predetermined amount.

3. An apparatus according to claim 2 wherein the controller comprises a transmitter configured to transmit signals relating to the one or more operating parameters to a controller of the debarker for adjusting the debarker for debarking the wood proximal to the sample portion.

4. An apparatus according to claim 3 wherein the one or more operating parameters includes a debarking force of the debarker.

5. An apparatus according to claim 4 wherein the transmitter is configured to transmit signals relating to the one or more operating parameters to a controller of a press roll assembly associated with the debarker.

6. An apparatus according to claim 5 wherein the one or more operating parameters includes a pressing force and/or a feed speed of the press roll assembly.

7. An apparatus according to claim 6 wherein the signals relating to the light image relate to a degree of brightness of the light image.

8. An apparatus according to claim 7 wherein the degree of brightness is rendered into greyscale or color values.

9. An apparatus according to claim 8 wherein the light image is divided into sections aligned with a direction of scraping of the scraper.

10. An apparatus according to claim 6 wherein the signals relating to the light image relate to a degree of dispersion of the light image.

11. A method for determining one or more operating parameters for debarking wood, the method comprising:
   (a) scraping with a scraping force a sample portion of wood to be debarked by a debarker, and generating a signal relating to the scraping force;
   (b) impinging light on a scraped surface of the sample portion;
   (c) detecting a light image defined by reflected light from the scraped surface, and generating a signal relating to the light image; and
   (d) determining one or more operating parameters based on the signals relating to the scraping force and signals relating to the light image, whereby the one or more operating parameters are relevant to debarking wood proximal to the sample portion.

12. A method according to claim 11 wherein step (d) comprises evaluating from the signals relating to the light image a degree of bark remaining on the scraped surface and determining the one or more operating parameters based on the signals relating to the scraping force when the degree of bark remaining falls below a predetermined amount.

13. A method according to claim 12 further comprising stopping step (a) when the degree of bark remaining falls below the predetermined amount.

14. A method according to claim 12 further comprising step (e) transmitting signals relating to the one or more operating parameters to a controller of the debarker and/or a controller of a press roll assembly associated with the debarker.

15. An method according to claim 14 wherein the one or more operating parameters is a debarking force of the debarker, a pressing force of the press roll assembly and/or feed speed of said sample portion.

16. A method according to claim 15 wherein step (c) comprises dividing the light image into sections aligned with a direction of the scraping.

* * * * *